(12) United States Patent  
Gurin (10) Patent No.: US 8,447,042 B2  
(45) Date of Patent: May 21, 2013

(54) SYSTEM AND METHOD FOR AUDIOMETRIC ASSESSMENT AND USER-SPECIFIC AUDIO ENHANCEMENT

(76) Inventor: Nicholas Hall Gurin, Manitou Springs, CO (US)

( * ) Notice: Subject to any disclaimer, the term of this patent is extended or adjusted under 35 U.S.C. 154(b) by 628 days.

(21) Appl. No.: 12/658,908

(22) Filed: Feb. 16, 2010

(65) Prior Publication Data

US 2011/0200217 A1     Aug. 18, 2011

(51) Int. Cl.
*H04R 25/00* (2006.01)

(52) U.S. Cl.
USPC .............................. 381/60; 381/58; 381/312

(58) Field of Classification Search ............. 381/56, 381/58, 60, 312, 314, 320, 321, 71.6, 103, 381/104; 600/559; 73/585
See application file for complete search history.

(56) References Cited

U.S. PATENT DOCUMENTS

| | | | |
|---|---|---|---|
| 4,548,082 A * | 10/1985 | Engebretson et al. | 73/585 |
| 6,118,877 A * | 9/2000 | Lindemann et al. | 381/60 |
| 2005/0094822 A1 | 5/2005 | Swartz | |

* cited by examiner

*Primary Examiner* — Huyen D Le  
(74) *Attorney, Agent, or Firm* — Galvin Patent Law LLC; Brian R. Galvin (57) ABSTRACT

According to a preferred embodiment of the invention, a system for audiometric assessment and user-specific acoustic enhancement, comprising an audiometry management module, a tone generator coupled to the audiometry management module and adapted to generate streams of acoustical output, and a hearing profile data file, is disclosed. According to the embodiment, the audiometry management module, in a plurality of sessions, instructs the tone generator to send a series of streams of acoustical output of varying acoustical intensity, and, on receiving a series of user responses responsive to audible perception of sounds generated from the streams of acoustical data, the audiometric management module determines, for each of a plurality of frequencies, a hearing threshold, and stores at least that threshold in the hearing profile data file.

6 Claims, 7 Drawing Sheets

SYSTEM AND METHOD FOR AUDIOMETRIC ASSESSMENT AND USER-SPECIFIC AUDIO ENHANCEMENT

BACKGROUND OF THE INVENTION

1. Field of the Invention

The present invention is in the field of audio processing and audiometry. More particularly, the present invention is in the field of enhancement of audio signals based on a particular user's hearing acuity profile.

2. Discussion of the State of the Art

Audiometry is used to test an individual's hearing ability, or acuity, and is normally performed by a professional audiologist. Typically, a device called an audiometer is used to determine a test subject's hearing levels. The test is designed to determine the threshold of audibility or the level of sound just audible to the test subject listener. This is a behavioral test in that the test subject must cooperate by listening carefully and signaling that the frequency played has been heard. Instructions are given concerning the test procedure, requiring the test subject to indicate the moment at which he can just hear or not hear a specific sound. Normally the test subject is asked to click a button or wave a hand as soon as the sound level becomes audible to him. Thus the lowest intensity sound they hear is recorded. Typically the ears are tested individually using earphones in an environment free from background noise. Both of the test subject's ears are tested through a range of frequencies, for example 0.5, 1, 2, 3, 4, 6, and 8 kHz. The hearing threshold is recorded for each frequency via a series of sound exposures with increasing volume. The technique enables a comparison of the individual's threshold of hearing at each frequency with a reference value. Another common set of frequencies used uses a series of frequencies an octave apart from each other, namely 125, 250, 500, 1000, 2000, 4000, 8000 Hz. From this data an audiogram or pictorial representation of hearing loss at various frequencies is produced.

The audiogram is a standard way of representing a person's hearing loss. Standard audiograms cover a limited range of around 100 Hz to 8000 Hz and plot the threshold of hearing relative to a standardized curve that represents "normal" hearing. Ideally the audiogram, when plotted, would be a straight line, but in practice everyone is slightly different and small variations are considered normal.

While the human ear is capable of resolving around 1500 frequencies, standard audiometry protocols typically involve tests of only six to eight frequencies, and are usually focused primarily on detecting significant hearing loss and allowing medical professionals to compensate sufficiently that the hearer is able to perceive speech reasonably well. This limitation in the art arose when technologies were less capable than today, and when restoring the ability to communicate well with others was as much as could be expected with available hearing aids. However, even people who are not diagnosed as "hearing impaired" will typically, over their lives, develop variations in hearing acuity that may interfere, for example, with their enjoyment of music. Testing only at six or eight frequencies will generally be effective in detecting medically significant hearing loss due, for example, to pathologies of the ear or brain, but they will not detect individual frequencies that have developed lower acuity than an individual's overall level. This can happen when a person is exposed, especially on a repeated basis, to exceedingly high levels of noise at a particular frequency (for instance, if a person works for years in the presence of machinery that gives off strong narrowband sound, especially if adequate hearing protection is not routinely used). Normally variations in hearing acuity are expected in individuals who are not considered to be suffering from hearing loss. It generally is not practical for an audiologist to test all available frequencies, and accordingly most audiometric standards, equipment, and protocols—and most hearing aids—are designed to test for, and compensate for, only hearing loss on a few standard frequencies. For these reasons, the audiometric standards in the art today are not suitable for assisting individuals, whether hearing-impaired or not, in improving hearing response for applications other than speech recognition. In particular, music enjoyment would be enhanced with a high-fidelity audiometric process that measures hearing acuity for many frequencies, and that can track changes over time and compensate for them. Furthermore, most audiometric results (as limited as they tend to be) are applied only for the tuning of hearing aids or dedicated devices, such as that disclosed in U.S. Pat. No. 7,564,979. Many people of advancing age continue to enjoy music using many playback systems, and need a way to adjust the quality of the playback to take into account their particular hearing profile in a rich way.

While hearing aid devices known in the current art do assist those with significant hearing pathology, they have a number of limitations and do not necessarily improve the quality of sound enjoyment for the listener. Many people with known minor hearing loss decline to use standard hearing aids due to embarrassment or due to the work and expense of maintaining and wearing the device. A very small percentage of the population actually benefits from the use of hearing aids. In general only those individuals who already know they suffer from hearing loss seek out an audiologist while a significant percentage of the population may have significant hearing deficits that go undiagnosed. As the "baby boomer" generation ages the percentage of individuals that could benefit from an audio enhancement method will only increase.

Advanced electronic audio sources have become ubiquitous in our society. Home theater sound systems for music, video and gaming are common and audio quality has become increasingly important. Mobile audio devices such as mobile phones, music players (for example, iPods), and car stereo systems have become standard fare for most individuals. Many individuals are not aware that their hearing is compromised for hearing various frequencies at various volumes. While some devices are equipped with manually regulated equalizers that can be adjusted by an individual to subjectively improve the sound, many are not, and most individuals never take the time to try to adjust standard equalizer settings. Standard equalizer settings are also (like audiograms) very limited as to the number of frequencies that can be adjusted so that their ability to improve the listening experience for an individual is limited. Moreover, while many devices have built-in equalizers (and there are some standalone equalizers available), only sound output coupled to any given equalizer benefits from the settings made by a user. When the same user uses a different piece of equipment, a completely new set of equalizer settings need to be entered. One means common in the art for simplifying the use of equalizers is to provide a plurality of pre-set equalizer adjustments, such as "Bass Reducer", "Bass Booster", "Classical", or "Acoustic". A shortcoming of these standard settings is that they do not account for, or compensate for, differences in hearing acuity among various individuals.

Audiophiles are individuals whose hobby is to seek high quality audio reproduction and are willing to seek out and pay for high-end audio electronics that come as close as possible to mimicking a live performance. An audiophile may or may not have specific hearing loss. These individuals with an acute sense of quality sound would also provide a market for any device that could custom equalize sound output for a plurality of devices in order to maximize their hearing enjoyment.

SUMMARY OF THE INVENTION

The current art of audiometry and the current art of electronic sound production have not come together to maximize sound quality for most users. The invention seeks to solve this problem by providing an audio enhancement method that includes a vastly more detailed hearing profile based on each individual's hearing acuity, and a method or methods to use the detailed hearing profile data in order to custom equalize produced sound for the benefit of individual listeners.

Audiometry as practiced in the art is primarily administered by professionals and primarily to those individuals with major hearing pathology. Currently available solutions have many limitations as described above. The invention provides a method to improve standard data used in audiograms by testing multiple frequency bins (that is, ranges of frequencies centered on particular frequency, which is considered the center of the "bin") during individual tests and combining results of particular test sessions into a composite data file for an individual test subject or group of test subjects. The invention also provides a method to account for differences in the frequency response of different audio playback devices, in order to enable them to be better adjusted to each listener's audio profile. The invention also seeks to break down barriers for many individuals, who may be reluctant to seek a solution from an audiologist because of a perception that the only solution is a hearing aid device worn on or inside the ear. While the invention could be used by professional audiologists in a traditional office setting, various embodiments that allow for self-generated or self-administered tests by end user test subjects in a home environment are also disclosed. The invention could be marketed to professionals and directly to end users as well. Because of the invention's ability to provide for ongoing testing over time and thereby to test vast numbers of different frequency combinations at different times, an extremely detailed custom hearing profile may be produced by the invention. This is an improvement over the current art of producing an audiogram using only six to eight standard settings, typically determined in one visit to an audiologist's office and then updated annually or even less often. Even if an initial assessment is done in a traditional audiologist setting, a client may, according to the invention, follow up professional testing with additional testing of the same and different frequency bins in a home environment by logging onto a website equipped with a network audiometry module manager. Note that an audiometry module manager, which could in various embodiments be a dedicated software module stored on and operating via the microprocessor of a general-purpose computer, or an application-specific integrated circuit embedded in a standalone device (as is well-known in the art of electronics), provides testing and collects hearing profile data. It may alternatively, in various embodiments, exist as a stand-alone device or reside on a network.

A computation module used in an embodiment of the invention collects data from a test subject and assembles multiple hearing profiles into one. When a frequency is checked multiple times, a computation module may be programmed to use a latest value, an average of values, or a predicted value based on a trend of change over time using one of a plurality of possible prediction algorithms including, but not limited to, linear extrapolation, polynomial spline extrapolation, or neural network prediction based on previous data.

The composite hearing profile produced by embodiments of the invention can exist on hardware such as a memory stick (using flash memory or another memory technology as may be or become available in the art), or it may be stored in a network. For example, in the case of a hardware device it could be physically inserted into a specifically equipped sound-producing device such as a home entertainment system, automobile sound system or a portable device such as a portable music player or a cell phone. The composite hearing profile, in some embodiments, is stored coresident with self-executing code such that, when the memory device on which it resides is inserted into a suitable port or fitting in a specialized or general-purpose computer, said code may be automatically executed (this process is well-known in the art of self-executing software modules on portable memory devices), and optionally act as a software-based equalizer that operates in tandem with existing playback software on the applicable computer, or optionally may interface with computer-resident sound playback software and upload or transfer into such computer-resident software the composite hearing profile for use in enhancing audio playback on the computer. In an embodiment a custom hearing profile module combines software and hearing profile data to provide custom equalization within a sound-producing device. Another embodiment enhances the function of a noise-cancelling system as a custom hearing profile module interacts with device equalizer settings according to a unique hearing profile data. An additional embodiment of the invention specifically modifies the volume of specific frequencies in response to ambient background noise. This embodiment further enhances a listener's hearing ability, for example when using a cell phone in a noisy environment.

According to other embodiments of the invention, custom hearing profile data is input over a network to a network-based custom equalizer module. This module can receive various inputs of audio over one or more networks and can deliver custom sound to compensate for a specific hearing profile of a particular listener. Such a method can deliver a custom sound-producing signal from a networked-based audio source such as iTunes™ or Internet radio stations, enabling an audio signal which can be played on a user's sound system directly or downloaded onto a device such as a portable music player or indeed any sound storage device, for later playback.

The end result in various embodiments is enhanced sound quality that specifically equalizes frequency output to specific optimal levels as determined by a given listener's (or group of listeners') hearing profile. This would not only be beneficial to those who are significantly hearing-impaired, but also would help those who may not be aware that they are not hearing certain frequencies at certain volumes. The invention could be perceived as valuable to the following customer types:

1. Hard of Hearing—This is a person with a significant hearing deficiency, who would normally seek out a professional audiologist for diagnosis and may already be using a hearing aid. The hearing loss causes him to not be able to appreciate music or other audio input as much as he would like. This individual would benefit from an audio enhancement method.

2. Hearing Compromised—This is a person who recognizes that he might have a bit of hearing loss, but that it is not disabling to the point of seeking help from an audiologist. Many in this category might shun the audiologist because they have negative connotations about use of hearing aids. This individual would be a prime consumer for an audio enhancement method.

3. Average Consumer—This person may have no perceptible hearing loss but may still appreciate the benefit from audio enhancement technology by its improvement of output from a favorite device by making the output more intelligible or pleasing.

4. Audiophile—This person makes it a hobby to carefully listen to music and to pursue perfection in reproduced sound. This person may or may not have discernible hearing impairment, but his perception of the sounds he listens to would be enhanced by customizing the output of his system to match his own personal hearing profile.

The invention provides an improved ability, relative to the prior art, to identify specific hearing impairments or sensitivities whether they are disabling, just a nuisance, or imperceptible. It also allows for ease of continual reassessment to monitor and adjust for progressive hearing loss. The audio enhancement method described herein is able to customize sound output of a myriad of devices to enhance and enrich the listening experience for the test subject listener and can continually readjust settings as the hearing profile changes.

According to a preferred embodiment of the invention, a system for audiometric assessment and user-specific acoustic enhancement, comprising an audiometry management module, a tone generator coupled to the audiometry management module and adapted to generate streams of acoustical output, and a hearing profile data file, is disclosed. According to the embodiment, the audiometry management module, in a plurality of sessions, instructs the tone generator to send a series of streams of acoustical output of varying acoustical intensity, and, on receiving a series of user responses responsive to audible perception of sounds generated from the streams of acoustical data, the audiometric management module determines, for each of a plurality of frequencies, a hearing threshold, and stores at least that threshold in the hearing profile data file.

In a further embodiment of the invention, a custom equalizer module adapted to modify an incoming audio stream by adjusting at least a plurality of the frequency components of the audio stream based on data stored in the custom hearing profile data file. In yet a further embodiment of the invention, the hearing profile data file is adapted for interoperation with more than one custom equalizer module. In another embodiment of the invention, the hearing profile data file is stored on a portable memory device. Further, according to an embodiment of the invention, the incoming audio stream is delivered over a network from a third-party source. Yet further, according to an embodiment of the invention, the custom equalizer module is stored in and operates within in a network-resident server computer and is accessible to end users across the network on which the server resides.

In another preferred embodiment of the invention, on measuring acoustical response to a given frequency for a given user during more than one session conducted at different times, the hearing threshold stored in the hearing profile data file is modified based at least in part on the time series generated by subsequent measurements of the given frequency.

In another preferred embodiment of the invention, a method of audiometric assessment and user-specific audio enhancement, comprising the steps of (a) under the direction of an audiometric management module, generating a series of acoustical output streams of varying amplitude for each of a plurality of frequencies from a tone generator and sending it to a user, (b) receiving test responses from said user responsive to audible perception for each frequency, (c) based on the received test responses for each frequency, determining at least a hearing threshold for each frequency, and (d) storing the generated hearing thresholds for each frequency in a hearing profile data file, is disclosed.

In a further embodiment of the invention, the method also comprises the steps of: (e) receiving an audio stream at a custom equalizer module, (f) adjusting at least a plurality of the frequency components of the audio stream based at least in part on the hearing thresholds stored in the hearing profile data file for the frequency components, and (g) sending the modified audio stream to a user.

DETAILED DESCRIPTION

Figure 1:
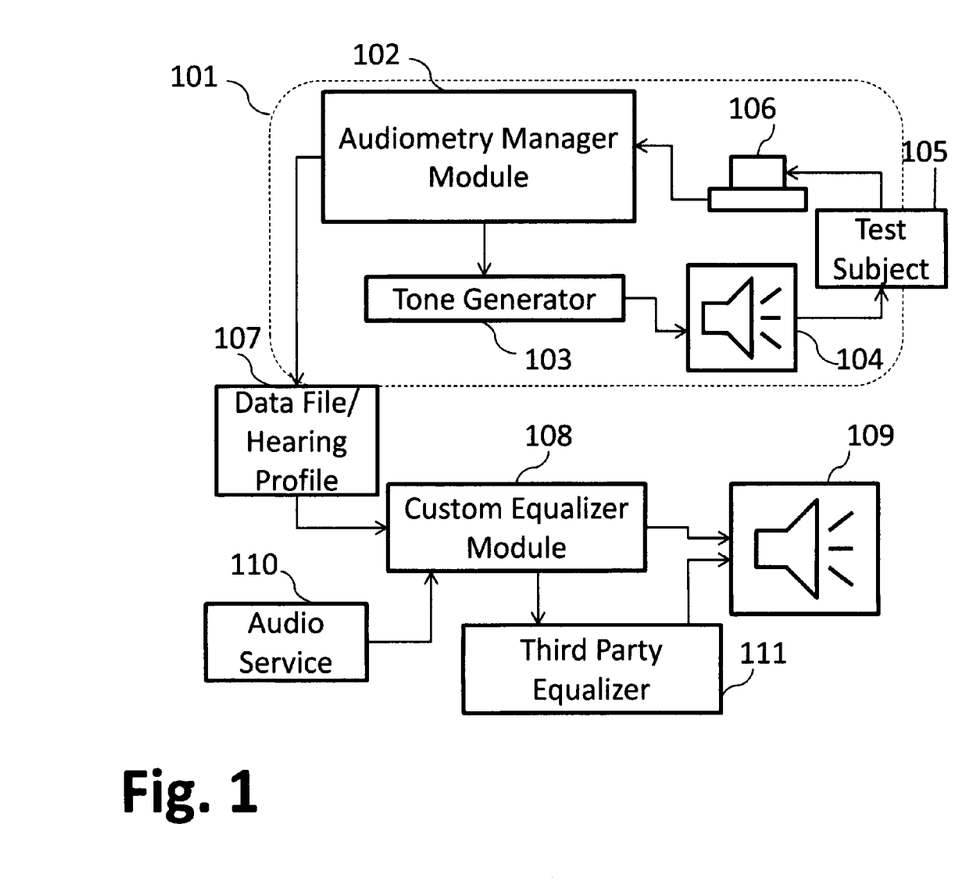
FIG. 1 is a schematic diagram of an embodiment of the invention comprising an audiometric system according to the prior art and a custom equalizer module.

FIG. 1 is a schematic diagram of an embodiment of the invention that includes an audiometric system 101 according to the prior art. In the prior art, an audiometry manager module 102 sends a signal to a tone generator 103, which, responsive to the signal, generates a tone of a specific frequency and volume, the tone then being transmitted or played through speaker system 104. Test subject 105 is instructed to manually deploy a signal generator 106 such as by pressing a button, depressing a foot pedal, or clicking a mouse, or signaling in some other way as soon as he hears an audible tone. Signal generator 106 then provides feedback to audiometry module 102 indicating that a specific frequency was audible to test subject 105. Results of a series of these tests are stored in data file 107, which in some cases is also printed out as a graphic representation of test results, known in the art as an audiogram. Data file 107, generated by this invention, will also be referred to herein as hearing profile data 107.

While the examples provided in this specification generally discuss "traditional" audiometric measurements, it is certainly possible, within the scope of the invention, to determine an individual's hearing sensitivity in other ways. For example, in one embodiment of the invention, an inverse approach is used, in which a person is played a tone and asked to provide an indication of when the tone ceases to be audible. In another embodiment of the invention, sensitivity is determined by receiving a plurality of indications pertaining to a subjective experience of sound by an individual, including but not limited to indications of "just became audible", "just became inaudible", "just loud enough", "just too loud", and the like. Any one of these, or other similar indications of personal audible perception, may be used according to the invention to establish a hearing profile. Moreover, in some embodiments a band of values, rather than a single value, is used to indicate a personal hearing perception. For example, a data pair consisting of "just loud enough" and "just too loud" measurements, as provided by a user based on the user's personal perception, can be used according to the invention to establish a range of acceptable levels for a given frequency of frequency band. These examples are merely to illustrate that any means of receiving indications from a plurality of individuals may be used, according to the invention, to establish a hearing profile.

Current industry standard audiograms only plot a limited standard number of frequencies (typically approximately eight distinct frequencies), and are used primarily to diagnose hearing pathology. However, the human ear is capable of detecting over 1500 individual frequencies. Data file 107 differs from prior art audiograms at least in that audiometry manager module 102 is capable of directing tone generator 103 to produce many individual frequencies. Because of increased granularity of test data achieved thereby, a much more sophisticated database or hearing profile 107 is generated according to the invention. This profile 107 is ideal not just for documenting hearing pathology but also, in various embodiments of the invention, can be programmed or uploaded into a custom equalizer module 108 so that output sound 109 from custom equalizer module 108 is manipulated specifically to compensate for hearing deficiencies of an individual test subject 105.

Audiometry manager module 102 can be a stand-alone device or can be network-based and accessible on or via a website. Custom hearing profile 107 may be generated by an audiologist, or by any other person including a test subject 105 himself. Likewise, custom equalizer module 108 may be a stand-alone device, or it can be network-based and accessible on or via a website. In either case any audio service 110, such as XM Radio, local radio stations, iTunes™, network-based programming, etc., may provide input to custom equalizer module 108, which then manipulates input audio according to custom hearing profile 107 specifications so that output sound 109 compensates appropriately for test subject's 105 hearing deficiencies. Adjustment is conducted using methods well-known in the art of sound equalizers, for example augmenting a sound signal in a frequency band around a center frequency which, according to a custom hearing profile 107, is deficient (has reduced aural acuity), with custom equalizer module 108 adjusting sound output by an amount that depends on the degree of hearing loss indicated by custom hearing profile 107 for the affected frequency. Where custom hearing profile 107 indicates a frequency of higher-than-normal acuity, custom equalizer module 108 would instead decrement sound inputs in a range around the affected frequency by an amount that is determined by the degree of "acuity excess". Because of higher granularity (typically although not necessarily many more than eight frequencies are measured for each user, according to the invention) in custom hearing profile 107, and in view of capabilities of custom equalizer module 108, output sound 109 provides an improved listening experience for test subject 105 as compared to any prior art using only a standard audiogram as data.

In another embodiment custom equalizer module 108 can provide data to a third-party equalizer 111 which manipulates a normal output sound into a custom output sound that compensates for a specific test subject's 105 custom hearing profile 107. Third-party equalizer 111 may be network-based (such as iTunes) or a stand-alone device designed specifically to receive data files and having a built in custom equalizer. Such device could be a cell phone, personal portable hearing aid, any portable sound system, automobile sound system, home entertainment system or any sound producing device that is programmed with a custom equalizer capable of receiving hearing profile data files 107.

Hearing profile data file 107 can be network-based or put onto a physical device such as a memory stick. It can be transferred over a network such as the Internet to any network-based third party site equipped with a custom equalizer module 108, or can be transferred to a physical sound producing device capable of receiving data files and programmed with a custom equalizer module 108.

In some embodiments of the invention, specific equipment characteristics of sound-producing equipment may be used to facilitate improved custom equalization according to the invention. For example, when playing a series of tones using tone generator 103, specific acoustic characteristics of tone generator 103, when known, may be used to adjust recorded sound thresholds up or down (based on the known acoustic characteristics). Thus, if tone generator 103 is known to be acoustically "weak" in a certain frequency range, any audiometric readings obtained in that range may be adjusted upwards to account for known variations in acoustic characteristics of tone generator 103. In some embodiments, users are provided with a facility to specify the sound producing device being used to test hearing, and acoustic characteristics of the identified device may be determined from a database lookup, an active query to a manufacturer, or any other data lookup means. In other embodiments, users of the invention are provided with a pre-calibrated microphone, which may be arranged physically in place of a user's ears in order to explicitly calibrate a sound-playing device to be used for audiometric purposes according to the invention. For instance, when a calibrated microphone is used to receive a test signal from tone generator 103, which is supposed to be of a certain acoustic intensity, a signal received from said microphone can be used to calibrate the acoustic characteristics of the sound-playing device 104 in use, thus facilitating adjustments to audiometric test results based on known (or calibrated) acoustic characteristics of tone generator 103. In another related embodiment of the invention, a range of audiometric readings may be taken using an unknown sound-playing device 104 and, when a calibrated set of readings for a specific user is already available, a set of acoustic characteristics of the unknown sound-producing device 104 may be inferred. When this approach is taken, it becomes possible to measure aural acuity of a given user using a wide variety of sound-producing devices 104 or tone generators 103 in order to provide maximum flexibility. In some embodiments, acuity-testing results from various sessions using various devices 104 are combined after taking into account any adjustments for acoustic characteristics of various sound-producing devices 104 used in testing. In other embodiments, separate composite hearing profiles 107 for each sound-producing device 104 are maintained so that specific adjustments based on a combination of user-specific aural acuity and device-specific sound-reproduction characteristics can be effected according to the invention.

Figure 2:
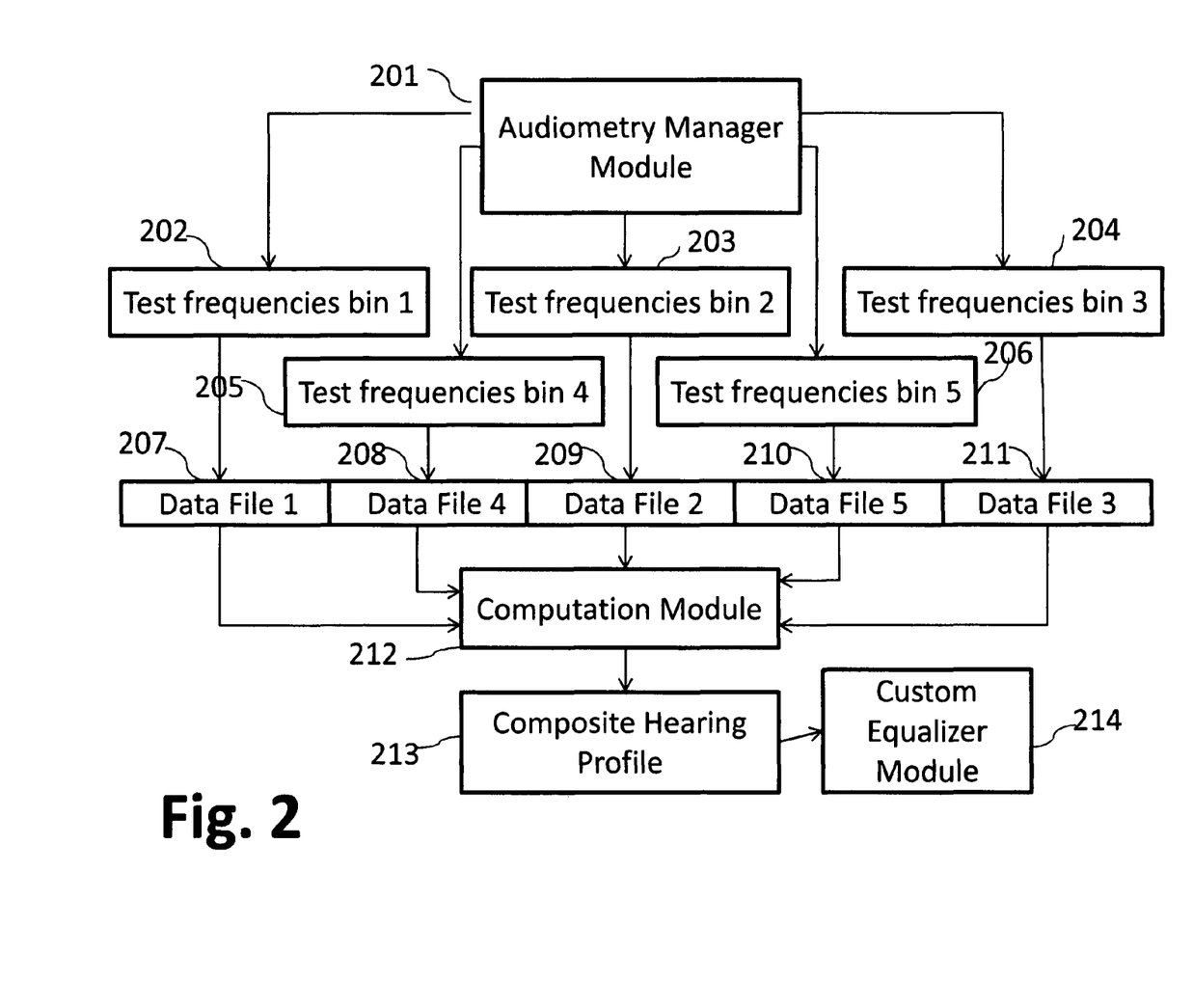
FIG. 2 is a block diagram illustrating an embodiment of the invention in which multiple sets of frequency bin measurements conducted over time are used to periodically or occasionally update a custom data file.

FIG. 2 is a block diagram illustrating the concept of using multiple sets of different frequency bins 202, 203, 204, 205, 206 over time to continuously (or periodically) update one or more composite hearing profiles 213. In this embodiment audiometry manager module 201 comprises an embedded signal source capable of producing and measuring many individual frequencies. Alternatively, a separate signal source can be controlled by audiometry manager module 201. Use of many different frequencies, optionally in different combinations, including some combinations consisting of some new and some repeat frequencies, allows an individual test subject 105 to be tested using different combinations of specific frequencies over time. Note that use of five test frequency bins 202, 203, 204, 205, 206 is for illustrative purposes only, and that the invention provides for numerous bins and is not limited to five; more or fewer distinct bins may be used according to the invention, and some bins may be repeated. For each bin tested an individual data file 207, 208, 209, 210, 211 may be recorded and inputted to the computation module 212, which combines new data for a test subject 105 with previous data from the same test subject 105. Alternatively, results from a plurality of test frequency bins 201-206 may be passed directly to computation module 212 and incorporated dynamically into composite hearing profile 213. The result is a composite hearing profile 213 that includes all or a selected portion of data about a given test subject 105, compiled by assembling all individual audiograms collected over time pertaining to a specific test subject 105 into one or more composite hearing profiles 213, or by assembling individual frequency test results received directly into a composite hearing profile 213.

Over time a given frequency may be checked multiple times, either in a previously tested bin that is retested, or in a new bin containing at least the same individual frequency. Computation module 212 can be manipulated in a number of ways. For instance, a latest test value for a given frequency could be used as the new value for that frequency in a new composite hearing profile 213. Alternatively, computation module 212 could average a set of test values for a given frequency, or even use a predicted value based on extrapolating from a trend of previous values over time for a given frequency or range of frequencies. Also because test data may be of high granularity, computation module 212 could produce time-dependent composite hearing profiles 213 based on values generated at various times in a day, or days of the week, or the like. In an embodiment of the invention audiometry manager module 102 can be network-based so that an individual test subject may have the convenience of having continual frequency assessments' updating his composite hearing profile 213 from the comfort of home. Composite hearing profile 213 can be stored on a physical device such as a memory stick or can be streamed directly to a network-based custom equalizer module 214 as previously described with reference to FIG. 1.

Figure 3:
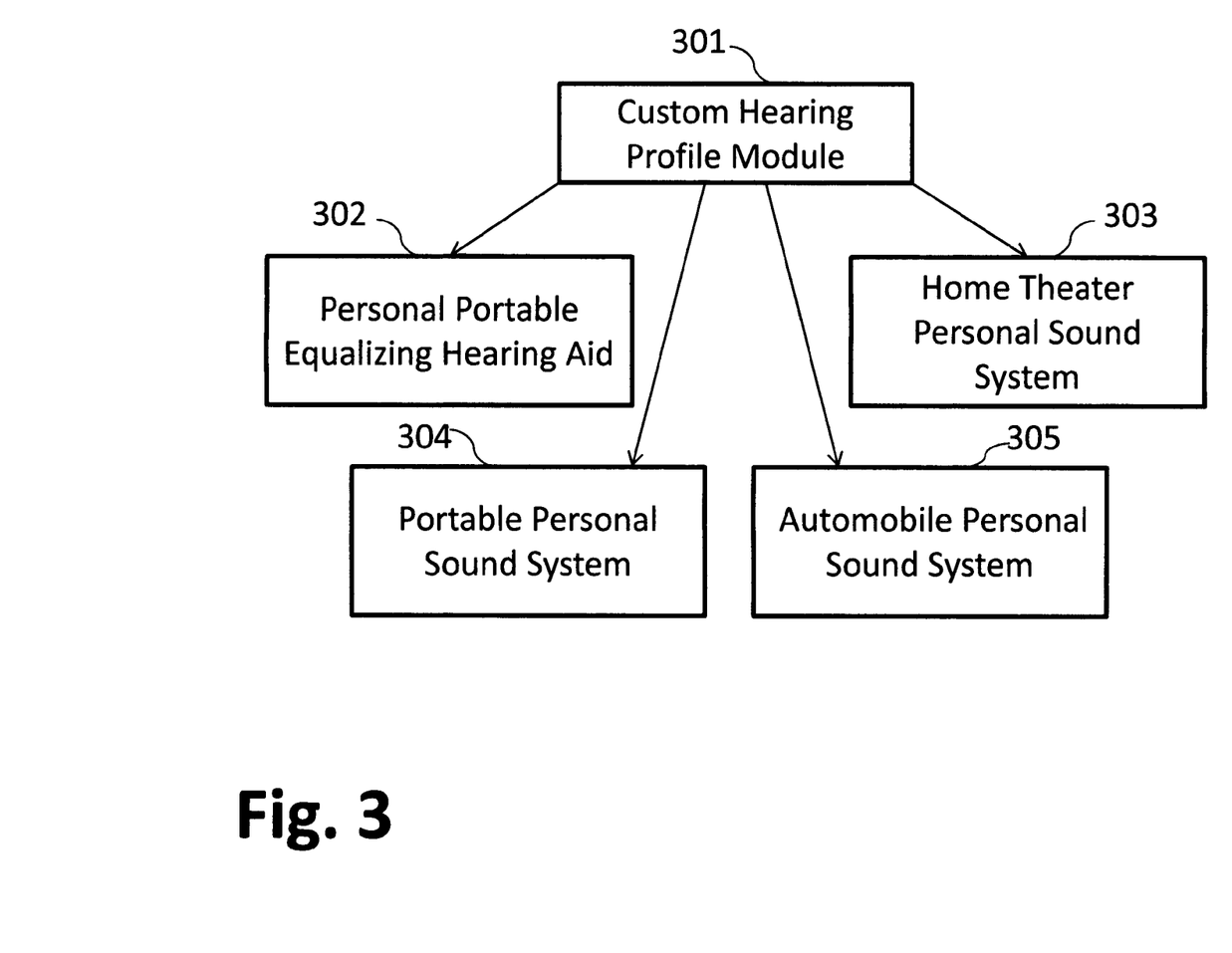
FIG. 3 is a block diagram illustrating an embodiment of the invention in which use of a custom hearing profile module to modify software within various sound systems results in altered output specific to the provided profile.

FIG. 3 is a block diagram of one embodiment illustrating use of a custom hearing profile module 301 to modify software within various sound systems resulting in altered output specific to custom data provided. Custom hearing profile module 301 contains composite data processed by computation module 212 and necessary software to interact and manipulate various devices such that sound equalization is altered by computation module 212. Audio modification is accomplished according to frequency-specific volume or power adjustments, as is common in the art of audio equalizer technologies. In some cases, devices affected by custom hearing profile module 301 may only be adapted for adjustments to specific frequency ranges. For example, in most portable audio playback systems, any equalizer provided adjusts the volume of each of about eight distinct frequency ranges, which collectively cover most or all of the audio frequency, or spectral range. Typically the audio spectrum range is divided into logarithmically equal ranges, often (but not necessarily) corresponding to central frequencies such as those described above. In such cases, custom hearing profile module 301 may, in some embodiments, average all frequency adjustments in a custom hearing profile that lie within each of the specific frequency ranges supported by the target device, in order to arrive at a single value for the range. Alternative means of determining a single value for a fixed frequency range are possible. For example, it may be desirable in some embodiments to give extra weight to one or more subranges (for example, the center of a frequency range could be weighted more heavily in averaging than extremes of the range). It should be appreciated by one having ordinary knowledge in the art that where a target device is capable of providing equalization for fewer frequency bands (or ranges) than are supported by custom hearing profile module 301, any means of determining a single value for each supported target frequency range may be used according to the invention. In some cases target devices will support uploading and execution of custom software. In these cases, software is uploaded, with either separate or encapsulated data, or both, from custom hearing profile module 301 to a target device, and executed within the target device. Such software will, in preferred embodiments, resolve an input audio signal within a target device into frequency ranges corresponding to a fullest level of detail supported by data from custom hearing profile module 301, and a signal for each corresponding frequency range is adjusted according to custom hearing profile 213 determined as described with reference to FIG. 1 or FIG. 2 and stored as hearing profile data in custom hearing profile module 301.

One such target device is personal portable hearing aid 302. By utilizing the audio enhancement method in one embodiment this device is programmed to maximum benefit by means of custom hearing profile module 301. Custom hearing profile module 301 updates equalizer settings in personal portable hearing aid 302, either via an internet connection in a network-based embodiment or via a device such as a memory stick or a USB cable that is inserted directly into the portable device. A user who may have progressive hearing changes could benefit greatly by having an easy way to continually update a personal portable hearing aid 302 over time. Custom hearing profile module could be used in similar ways with any portable personal sound system 304 equipped to receive data, such as a cell phone, iPod, MP3 player, or a similar device. An additional embodiment would allow for customization of an automobile personal sound system 305 and a home theater personal sound system 303. In all of these examples quality of sound would be improved for each individual test subject 105. An embodiment of the invention could include a reset function that restores original settings when desired; additionally, another user with her own custom hearing profile module 301 could insert her personal data as well. Another embodiment would allow for storage of multiple test subject 105 data on one custom hearing profile module 301 so that custom data could easily be changed for a shared sound-producing device.

Figure 5:
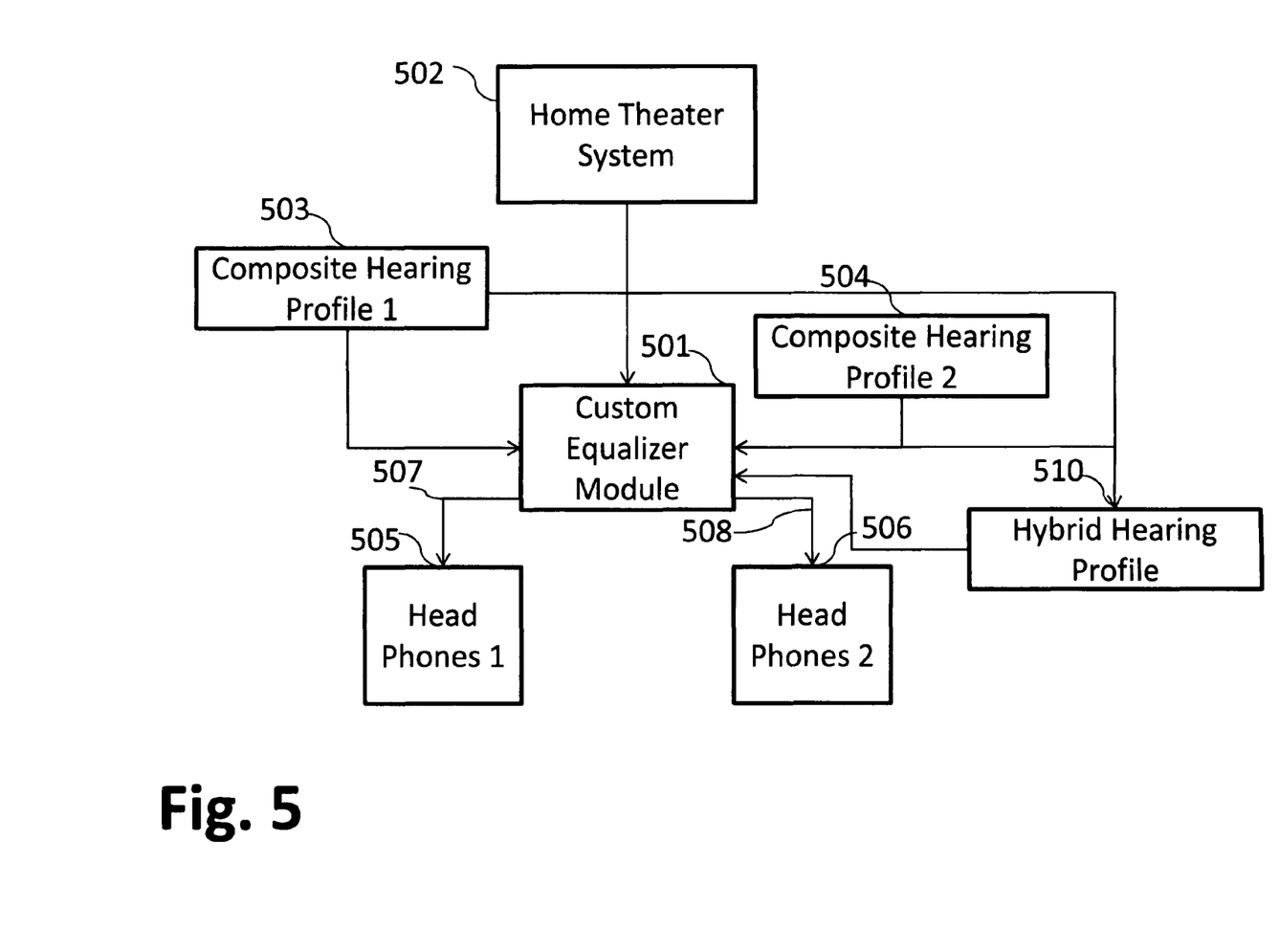
FIG. 5 is a block diagram illustrating an embodiment of the invention that utilizes multiple custom audio profiles resulting in multiple outputs of custom audio.

According to the invention, multiple custom hearing profiles 503, 504 can be stored in custom hearing profile module 301 within a memory region integral to a personal portable hearing device, or they may be stored in custom hearing profile module 301 residing on a separate piece of electronic equipment, such as a memory stick or a personal digital assistant, or any of the many highly portable means of storing digital data on or near one's person that are available in the art. When custom hearing profile module 301 resides physically separately from personal portable hearing aid 302 or other playback system such as for example those shown in FIG. 3, data resident in custom hearing profile module 301 may be transferred to said playback devices using a wireless technology such as BlueTooth, or a cable such as a USB cable or an audio headphone cable, or any of the many means well-known in the art for transferring data from one device to another, without departing from the scope of the invention. For instance, in one embodiment users of personal portable hearing aids are provided with an application resident on one of the many commonly available handheld computing devices known in the art, such as iPhone™ or a personal digital assistant, such that a user may, on the computing device, change or adjust custom hearing profile module 301 settings (such as by selecting a particular preset hearing profile from among a plurality of profiles stored on the computing device), and cause the selected profile to be loaded into the personal portable hearing aid 302 (or another playback device) by one of the means just discussed.

Note that the invention is not intended only for subjects with significant hearing loss or pathology, but also for individuals who are only hearing-compromised and may not need the benefit of an in-ear hearing aid but would treasure the richness of music and sound adjusted to their unique hearing deficiencies. Additionally, any person can measure his hearing acuity according to the invention and use a resulting composite hearing profile 107 to adjust quality of playback of an arbitrary audio signal. A person with no known hearing deficits but whose hobby is carefully listening to music and pursuing perfection in reproduced sound would benefit also from using such sound producing devices enriched by the audio enhancement method. An embodiment of the invention specifically increases volume of specific frequencies in response to ambient background noise. This embodiment further enhances the listener's hearing ability for example when using a cell phone in a noisy environment. In some embodiments, standard presets are provided for commonly encountered background noise situations, such as airports, interiors of commercial aircraft, regions of high automotive or other traffic, busy restaurant, and the like, in order to allow a user of the invention to select (via a switch, or a portable electronic device integrated with personal portable hearing aid and adapted to allow such adjustments; those having ordinary skill in the art will appreciate that there are many means of providing a user with a selection capability, and any of these may be used according to the invention) a particular environmental preset. When such an environmental preset is selected, custom hearing profile 503 is modified directly by frequency-specific or overall settings of the environmental preset. As discussed below with reference to combining two or more custom hearing profiles into a single custom hearing profile (or hybrid hearing profile 510), there are many well-known ways to combine such data elements according to the art, without departing from the scope of the invention.

Certain types and levels of hearing loss can cause some individuals to experience discomfort or hear "rattling" when certain frequencies are received by the ear in sufficient volume. The use of an audio enhancement method according to the invention, in conjunction with personal sound systems 302, 303, 304, 305 would keep volume of those specific frequencies below any threshold that triggers discomfort or "rattle" noise by modifying an output from a device. Accordingly, in some embodiments of the invention, in addition to volume adjustment levels for a given frequency band, thresholds are stored which reflect maximum allowable volumes for a particular user to ensure that no rattling or annoying noises are perceived by a particular user.

Figure 4:
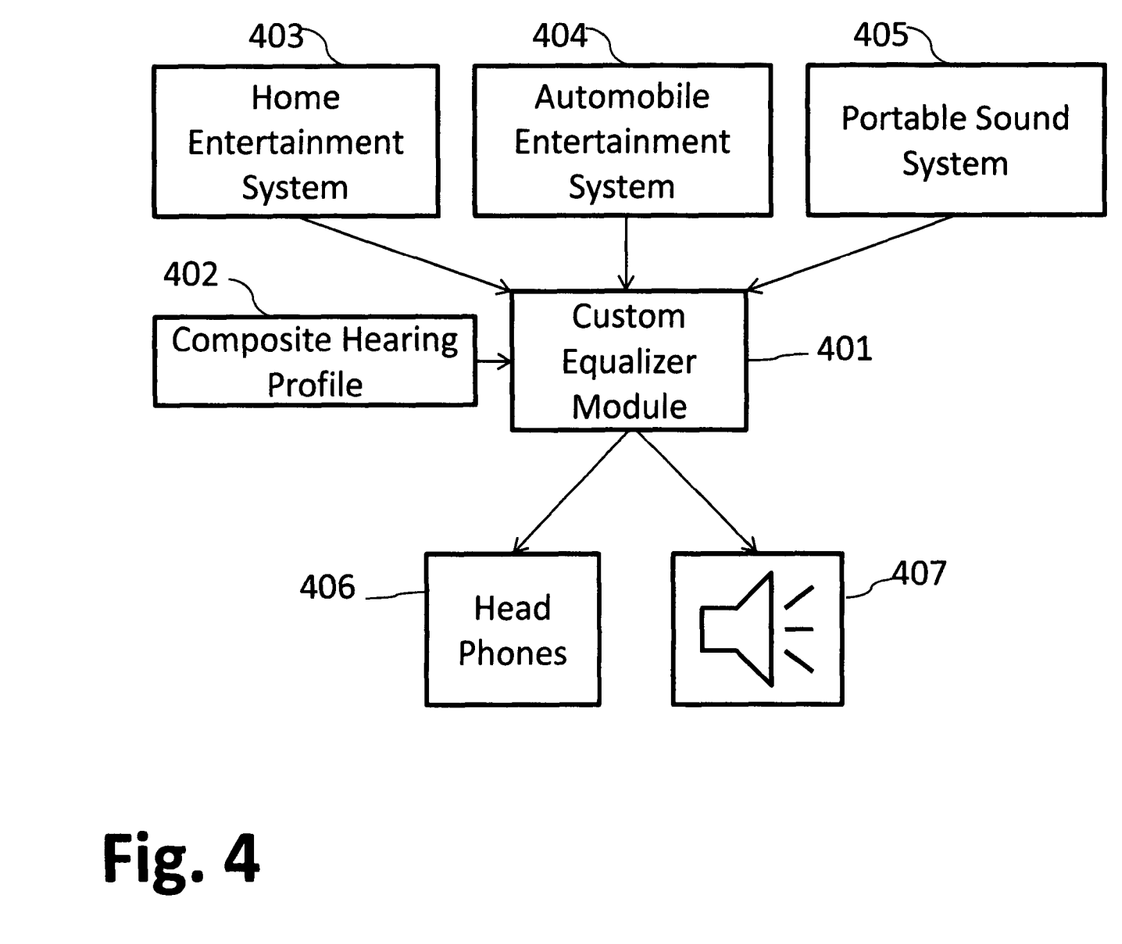
FIG. 4 illustrates an embodiment of the invention in which a custom equalizer module receives input from various audio sources and modifies audio output as directed by a custom data file.

FIG. 4 illustrates an embodiment in which custom equalizer module 401 receives input from various audio sources 403, 404, 405 and modifies a received audio signal before sending it to audio generator 406, 407 (that is, speakers, headphones, or the like) as directed by composite hearing profile 402. Note that audio sources in this diagram are for illustrative purposes only, as the invention is not limited to use by these sources but could receive input from any device that produces an audio source signal. Additionally, it is not required, according to the invention, that audio sources 403, 404, 405, or their equivalents, are located in the same device or place as custom equalizer module 401 or audio playback means 406, 407, or the like. For example, a network audio streaming source could deliver an audio stream over a network such as the Internet to custom equalizer module 401, which could be a specialized equalizer software executing on a general-purpose or a specially-designed computer, and sending a modified audio stream on to a audio playback device 406, 407 which could itself be operating on another computer or a dedicated playback device. Custom equalizer module 401 is, in some embodiments, a network-based audio stream "middle man" service that adjusts an incoming stream according to each individual user's personal audio profile and connects a modified audio stream to a suitable playback device. In some embodiments, a storage device is used to store modified audio for later playback; for example, a user could subscribe to a network service which helps her self-assess her hearing and then tailor online audio or video content to her particular hearing profile, storing results as personalized audio or video files that can be played in unmodified playback devices. This type of arrangement, according to the invention, is particularly useful when playback devices are not equipped with equalization capabilities, or when playback devices are very portable. In an embodiment of the invention, audio source's 403, 404, 405 output data is connected to custom equalizer module 401. Custom equalizer module 401 may reside in a network or may be a physical device. A custom equalized sound signal is then sent on to an audio generator such as a speaker system 407 or headphones 406 which then produces sound adjusted to a listener's specific composite hearing profile 402.

FIG. 5 is a block diagram illustrating an embodiment utilizing multiple custom audio profiles 503, 504 resulting in multiple simultaneous outputs 505, 506 of custom audio for multiple test subject listeners. Two simultaneously customized audio profiles are shown for illustrative purposes only. Other embodiments of the invention could have any number of profile inputs and audio outputs. In one embodiment an audio signal from a standard home theater sound system 502 is directed to a custom equalizer module 501 capable of processing multiple composite hearing profiles 503, 504. Again composite hearing profiles 503, 504 may reside on a network, a general-purpose computer, or on any suitable local physical device. Custom equalizer module 501 may also reside on a network or on (or as) a local physical device. In either case, custom equalizer module 501 equalizes an audio input signal according to data specified by one or more composite hearing profiles 503, 504. Custom equalized individual signals 507, 508 are then individually sent to headphones 505, 506 for listening by individual test subjects. Other means of audio playback may of course be used as well, such as personal speaker sets for example situated favorably for individual audio experience, as for example by having a small speaker on each of the left and right sides of a home theater seat's headrest. It should be appreciated by one having ordinary skill in the art that any number of well-known playback means are available in the art for conducting personalized audio signals to each listener in a home theater or similar listening environment.

In another embodiment of the invention, more than one custom hearing profiles 503, 504 are used together to create a joint listening experience, which is different from using a single device to play separately modified audio streams 505, 506 to individual users. According to the embodiment, custom hearing profiles 503 and 504 are combined to create a new custom hearing profile, which can then be used to modify a single audio stream being delivered to more than one user simultaneously. For example, if two people desire to view a video from a single system, and do not have (or want to use) separate audio playback devices, they could choose not to use the customer hearing profile 503, 504 of one or the other, or an unmodified audio stream, as any of these choices would result in one or the other user's (or both) having a substandard audio experience. According to the invention, more than one custom hearing profiles 503, 504 can be combined into a single hybrid hearing profile 510, which can then be loaded into custom equalizer module 501 and used to modify an incoming audio stream from (for example) home theater system 502 in a fashion that is satisfactory to both listeners. The act of combining two custom hearing profiles 503, 504 into a single hybrid hearing profile 510 can be accomplished in many ways, according to the invention. For example, for each of a plurality of frequency bins represented in the plurality of custom hearing profiles 503, 504, an average modification calculated by determining an average (weighted or not) of the more than one custom hearing profiles 503, 504 (it should be understood that while two custom hearing profiles 503, 504 are shown for exemplary purposes, any number of custom hearing profiles 503, 504 can be combined according to the invention). In another embodiment, an average overall modification is calculated for each custom hearing profile 503, 504, representing an average overall loudness adjustment across all frequencies (or across certain frequency ranges, which could for example be user-selectable), and hybrid hearing profile 510 could be baselined at the average overall level so calculated. Then, according to the embodiment, particular frequencies may be selected from each of the custom hearing profiles 503, 504, for instance by selecting only frequencies that deviate from the particular custom hearing profile's local amplitude average, and applied to hybrid hearing profile 510. In some embodiments, this frequency-specific adjustment is made by directly importing an offset percentage from the host custom hearing profile and applying it to the corresponding frequency in hybrid hearing profile 510. In other embodiments, such frequency-specific adjustments may be modified, for example by multiplying them by a real number between 0 and 1, to provide a modicum of adjustment to the listener from whose custom hearing profile 503 the frequency modification was drawn, while not overly distorting audio experience for other listeners more than necessary. It should be appreciated by one having ordinary skill in the art that there are many ways of combining more than one custom hearing profile 503, 504 into a single hybrid hearing profile 510, without departing from the spirit or scope of the invention.

Figure 6:
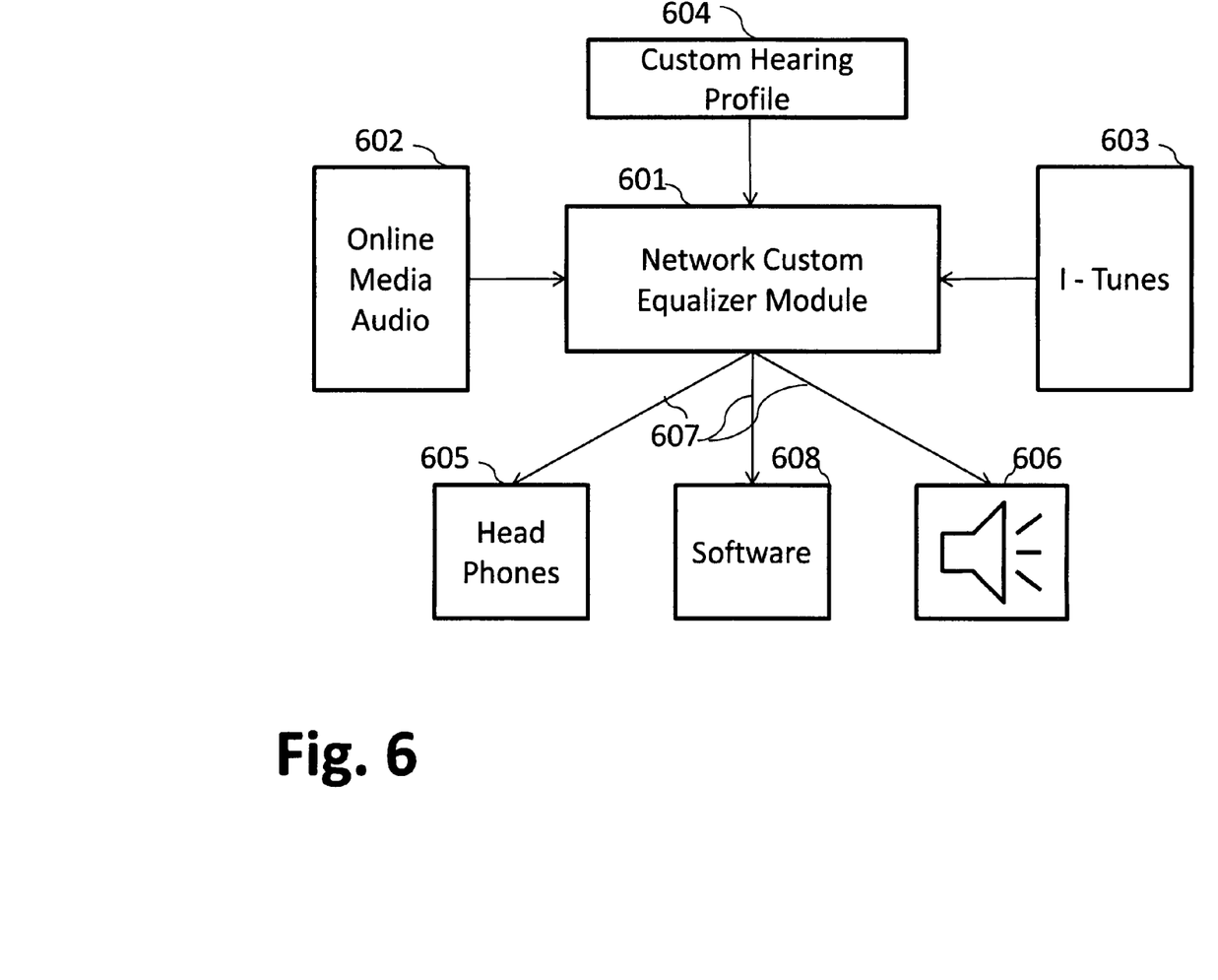
FIG. 6 illustrates an embodiment of the invention in which a system according to the invention is deployed over a network.

FIG. 6 illustrates an embodiment of the invention whereby the systems or methods of the invention are deployed over a network. Here a network custom equalizer module 601 receives data from one or more custom hearing profiles 604 over a network such as the Internet or a home entertainment network. Input is also received from one or more network audio sources 602, 603. A network audio source such as music on demand (for example, iTunes™) 603 or any other online media audio is sent over a network to network custom equalizer 601, which custom equalizes sound to compensate for a specific test subject's deficits, as found in the test subject's custom hearing profile 604. Custom signal 607, that is, a signal representing an original audio signal modified by application of listener-specific adjustments specified by network custom equalizer module 601, is then sent to speaker system 606 or personal headphones 605, or any other suitable audio playback device (it should be noted that, wherever an audio playback device is specified within this document, it is not intended to be exclusive; a video playback device that also plays back associated audio can also be used according to the invention, with only audio signal streams being affected by network custom equalizer module 601 or its equivalents). Alternatively, custom signal 607 could be downloaded into software 608 such as Windows Media Player™ or directly to a portable music or video player such as an iPod™ or MP3 player, for example. Custom equalized sound files could be stored on a personal computer and later downloaded into a test subject's 105 cell phone, portable audio playback device, or any other personal sound system capable of playing these audio files.

Figure 7:
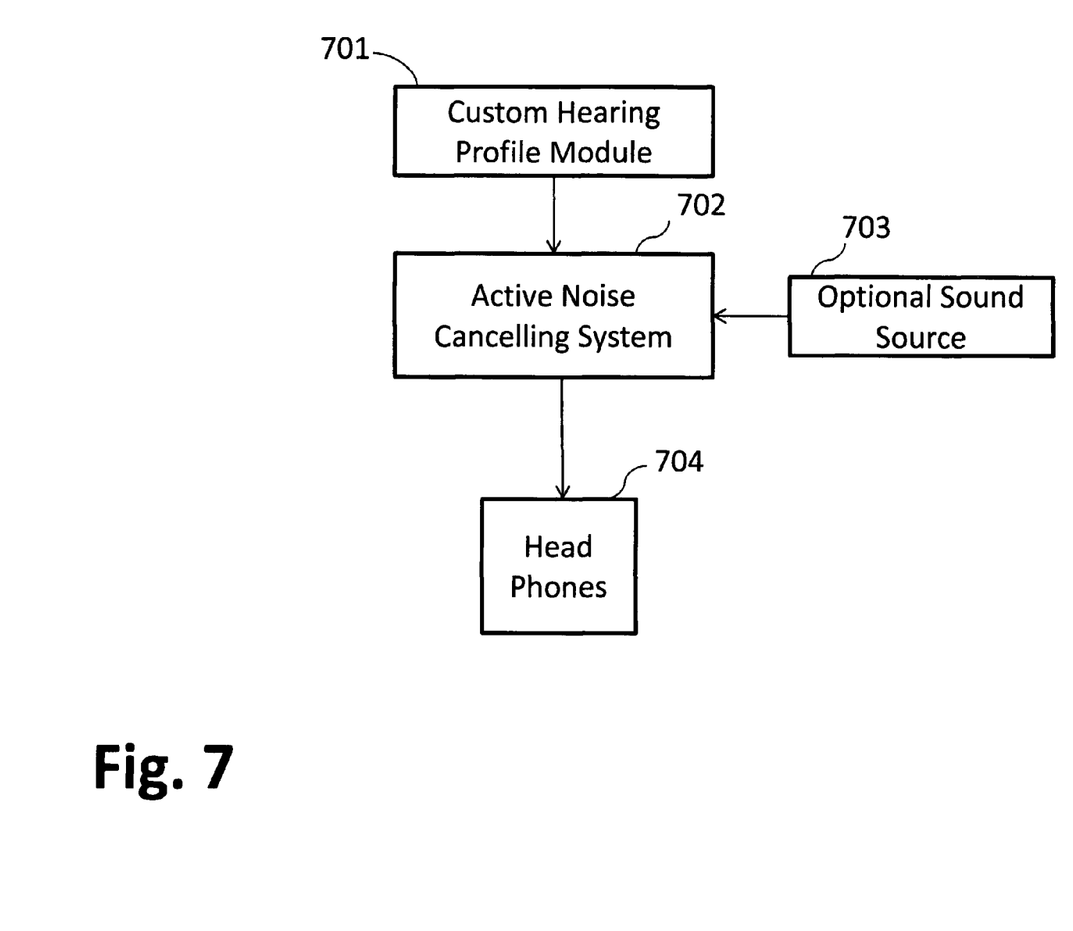
FIG. 7 is a diagram showing an embodiment of the invention in which an active noise cancelling system is improved for an individual by additionally carrying out an audio enhancement method.

FIG. 7 is a diagram showing an embodiment of the invention whereby an active noise cancelling system 702 is improved for an individual by employing an audio enhancement method according to the invention. In an embodiment, a custom hearing profile module 701 updates equalizer settings within an active noise cancelling system 702 to specifications of a user's specific hearing profile data. Any optional audio source input 703 would likewise have equalizer settings modified by custom hearing profile module 701. Custom hearing profile module 701 can reside in a network and update an active noise cancelling system 702 through an Internet connection, or custom hearing profile module 701 may be stored in, and execute on, a device that can be inserted or connected in some way to an active noise cancelling system 702. The resulting custom-corrected output to a test subject's headphones 704 could greatly improve the performance of an active noise cancelling system 702.

All of the embodiments outlined in this disclosure are exemplary in nature and should not be construed as limitations of the invention.

What is claimed is:

1. A system for audiometric assessment and user-specific acoustic enhancement, comprising:
    an audiometry management module;
    a tone generator coupled to the audiometry management module and adapted to generate streams of acoustical output;
    a hearing profile data file; and
    a custom equalizer module adapted to modify an incoming audio stream by adjusting at least a plurality of the frequency components of the audio stream based on data stored in the custom hearing profile data file;
    wherein the audiometry management module, in a plurality of sessions, instructs the tone generator to send a series of streams of acoustical output of varying acoustical intensity;
    wherein, on receiving a series of user responses responsive to audible perception of sounds generated from the streams of acoustical data, the audiometric management module determines, for each of a plurality of frequencies, a hearing threshold, and stores at least that threshold in the hearing profile data file; and
    further wherein, on measuring acoustical response to a given frequency for a given user during two or more sessions conducted at different times, the hearing threshold stored in the hearing profile data file is modified based at least in part on a time series derived from measurements of the given frequency during each of the two or more sessions.

2. The system of claim 1, wherein audio from a single audio source is delivered to a first user and a second user simultaneously using a first custom equalizer and a hearing profile data file for the first user and a second custom equalizer and a second hearing profile data file for the second user, thus delivering audio from a single audio source simultaneously to two different users with each user receiving audio that has been compensated for each user's specific hearing profile.

3. The system of claim 1, wherein a prediction of a user's hearing profile for a given frequency is made based on extrapolation of a time series of previous measurements obtained during two or more sessions of the user's hearing profile for the given frequency.

4. A method of audiometric assessment and user-specific audio enhancement, comprising the steps of:
   (a) under the direction of an audiometric management module, generating a series of acoustical output streams of varying amplitude for each of a plurality of frequencies from a tone generator and sending it to a user;
   (b) receiving test responses from said user responsive to audible perception for each frequency;
   (c) based on the received test responses for each frequency, determining at least a hearing threshold for each frequency;
   (d) measuring acoustical response to a given frequency for a given user, as described in steps (a) through (c), during two or more sessions conducted at different times and determining a modified hearing threshold for the given frequency based at least in part on a time series derived from measurements of the given frequency during each of the two or more sessions;
   (e) storing the generated hearing thresholds for each frequency in a hearing profile data file;
   (f) receiving an audio stream at a custom equalizer module;
   (g) adjusting at least a plurality of the frequency components of the audio stream based at least in part on the hearing thresholds stored in the hearing profile data file for the frequency components; and
   (h) sending the modified audio stream to a user.

5. The method of claim 4, wherein audio from a single audio source is delivered to a first user and a second user simultaneously using a first custom equalizer and a hearing profile data file for the first user and a second custom equalizer and a second hearing profile data file for the second user, thus delivering a audio from a single audio source simultaneously to two different users with each user receiving audio that has been compensated for each user's specific hearing profile.

6. The method of claim 4, further comprising the step of predicting a user's hearing profile for a given frequency based on extrapolation of a time series of previous measurements obtained during two or more sessions of the user's hearing profile for the given frequency.

* * * * *